United States Patent [19]

Rappoldt et al.

[11] Patent Number: 4,601,855
[45] Date of Patent: Jul. 22, 1986

[54] METHOD OF PREPARING 9β, 10α-5,7-DIENE STEROIDS

[75] Inventors: Menso P. Rappoldt; Gerardus H. M. Mos, both of Weesp, Netherlands

[73] Assignee: Duphar International Research B.V., Weesp, Netherlands

[21] Appl. No.: 701,018

[22] Filed: Feb. 12, 1985

[30] Foreign Application Priority Data

Feb. 15, 1984 [NL] Netherlands ............... 8400482

[51] Int. Cl.$^4$ ................. C07J 21/00; C07J 9/00
[52] U.S. Cl. ................. 260/239.55 C; 260/397.2
[58] Field of Search ............ 260/397.2, 239.55 C

[56] References Cited

U.S. PATENT DOCUMENTS 4,388,242 6/1983 Malatesta et al. ............ 260/397.2

Primary Examiner—Elbert L. Roberts
Attorney, Agent, or Firm—Stevens, Davis, Miller & Mosher

[57] ABSTRACT

The invention relates to the preparation of 9β,10α-5,7-diene steroids by irradiating the corresponding 9α,10β steroids with filtered ultraviolet light of an antimony lamp.

6 Claims, No Drawings

METHOD OF PREPARING 9β, 10α-5,7-DIENE STEROIDS

The invention relates to a method of preparing 9β,10α-5,7-diene steroids by irradiating the corresponding 9α,10β-steroids with filtered ultraviolet light.

9β,10α-5,7-diene steroids generally are intermediates in the synthesis of pharmacologically interesting compounds which can fulfil a useful function in the human body. The hormone-analogue 6-dehydro-9β,10α-progesterone (9β,10α-pregna-4,6-diene-3,20-dione) or dydrogesterone is an orally active progestative hormone and is generally used to correct deficiencies of progesterone in the body.

Therefore, a good possibility for synthesizing this substance and other 9β,10α-steroids from available or readily available raw materials is of great importance. Various 9α, 10β-steroids, for example, ergosterol, pregnenolone and 7-dehydrocholesterol, are available as raw materials for the preparation of 9β, 10α-5, 7-diene steroids. The preparation of dydrogesterone from pregnenolone is described by Rappoldt et al. in Recueil trav. chim. 80,43 (1961) and 90, 27 (1971). Important intermediates in the synthesis of dydrogesterone are lumisterol$_2$, 3-(ethylenedioxy)-9β,10α-pregna-5,7-diene-20-one and 3,20-bis(ethylenedioxy)-9β,10α-pregna-5,7-diene. These intermediates can be prepared by irradiating the corresponding 9α,10β-isomers, namely ergosterol, 3-(ethylenedioxy)-9α,10β-pregna-5,7-diene-20-one and 3,20-bis(ethylenedioxy)-9α,10β-pregna-5,7-diene, respectively, with ultraviolet light. This irradiation is preferably carried out with filtered ultraviolet light. A high-pressure mercury lamp has so far been used for this purpose. In the above-mentioned publications, the desired 9β,10β-5,7-diene steroids were formed during this photochemical isomerisation in yields of only 20% calculated on converted 9α,10β-isomer. When the UV-irradiation was carried out in two steps, namely first by means of short-wave and then by means of long-wave UV-radiation as described in Netherlands Patent Specification 112,521, the desired 9β,10α-5,7-diene steroid could also be isolated only in a yield of not yet 20% calculated or converted starting material. Obviously, a considerable part of the expensive starting material is lost in this photochemical isomerisation probably due to the formation of undesired side products. It therefore stands to reason that an improvement of the yield in this photochemical conversion is of great importance.

One has recently succeeded to considerably improve the conversion of ergosterol into pre-ergocalciferol or previtamin D by means of laser photolysis. Dauben and Phillips (J.Am.Chem.Soc. 104, 355 and 5780,1982) state that, by means of laser irradiation at higher wavelengths, more lumisterol$_3$ is formed from 7-dehydrocholesterol at the expense of previtamin D$_3$, i.e. that at higher wavelengths the formation of the 9β,10α-isomer is favoured. According to these authors, for example, it is possible to obtain 25% lumisterol$_3$ and 50% previtamin D$_3$ (in addition to 10% tachysterol) by using laser light of 305 nm, and even equally large quantities of these isomers, namely approximately 45%, by using laser light of 355 nm. A yield of 9β,10α-steroid, for example, lumisterol$_3$, of approximately 45%, however, is generally considered insufficient for industrial production. In addition, the results of Dauben and Phillips do not correspond to those of Malatesta et al. (J.Am.-Chem.Soc. 103, 6781, 1981). Although in this article a proviso is made as regards the completeness of the photo-equilibration, the results just indicate a dramatic decline of the yield of lumisterol when irradiated with laser light of higher wavelength, namely a reduction in yield to below 10% at 337 and 353 nm. Nor does U.S. Pat. No. 4,388,242 in the name of Malatesta et al. comprise any indication that lumisterol could be formed in a yield attractive for practice when irradiated with laser light. Moreover, for a practical industrial production the use of lasers is not very attractive in connection with the high costs of acquisition and the high energy consumption. Irradiation with a lamp is therefore to be preferred by far to laser irradiation for producing a given photochemical conversion.

It was surprisingly found that the photochemical conversion of 9α,10β-steroids into the corresponding 9β,10α-isomers occurs with a considerably higher yield when an antimony lamp is used as a light source instead of a laser or the conventional high-pressure mercury lamp. Depending on the structure of the starting material, a considerable improvement of the yield can be obtained thereby, even an improvement by over 200% compared with the irradiation with light of a high-pressure mercury lamp. An additional advantage is that the improvement of the yield is associated with the formation of a smaller quantity of by-products, as a result of which the purification of the desired product is facilitated. The irradiation may be carried out entirely with an antimony lamp or—which provides equally good results—first with a conventional light source producing UV-radiation, for example a high-pressure mercury lamp, after which the chemical conversion is completed by irradiation with an antimony lamp.

An antimony lamp is a gas discharge lamp in which the antimony present produces an emission spectrum during the discharge. Antimony lamps are also recommended for sterilization purposes.

In principle, all 9α,10β-5,7-diene-steroids may be used as starting materials for the photochemical conversion, provided preferably photosensitive substituents in the molecule are protected. For example, it is usually desired to ketalize ketone functions optionally present in the starting material, before subjecting the material to a photochemical conversion according to the invention.

However, the method according to the invention relates in particular to the preparation of 9β,10α-5,7-diene steroids from starting steroids of the general formula

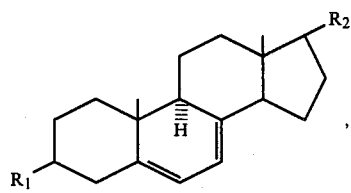

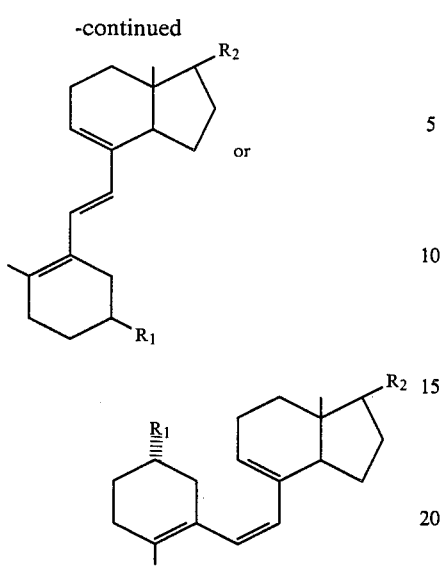

wherein $R_1$ is a hydrogen atom; an etherified, non-etherified, esterified, or non-esterified hydroxy group; or a ketalized or non-ketalized oxo group; and $R_2$ is a branched or non-branched, saturated or unsaturated hydrocarbon chain having at most 10 carbon atoms which, if desired, is substituted with one or more fluorine atoms, etherified, non-etherified, esterified or non-esterified hydroxy groups, and/or ketalized or non-ketalized oxo groups.

Examples of suitable starting steroids which play a part as an intermediate in the preparation of dydrogesterone are ergosterol and 9α,10β-3,20-bis(ethylenedioxy)-5,7-pregnadiene. As will become apparent from the examples, these compounds can be converted into the desired 9β,10α-isomers, namely lumisterol$_2$ and 9β,10α-3,20bis(ethylenedioxy)-5,7-pregnadiene, respectively, in so far unprecedentedly high yields. Other suitable starting materials are previtamins and tachysterols. For example, by using the method according to the present invention, previtamin D$_3$ can be converted into lumisterol$_3$ in a high yield.

The invention will now be described in greater detail with reference to the ensuing specific examples.

EXAMPLE I

Preparation of 9β,10α-3,20-bis(ethylenedioxy)-5,7-pregnadiene 20.0 g of 9α,10β-3,20-bis(ethylenedioxy)-5,7-pregnaidene were dissolved in 2 liters of tetrahydrofuran to which 2 drops of collidine had been added. The resulting solution was then irradiated with a Q2017 antimony lamp (brand Heraeus) while cooling and in a nitrogen atmosphere. As filters were used: a filter which absorbs all the light below 260 nm for 2.5 hours succeeded by a filter which absorbs all the light below 300 nm for 3.5 hours. Finally a solution was obtained, the dissolved substance of which according to HPLC-analysis is composed as follows: 54.2% (=10.84 g) of starting material, 5.5% (=1.10 g) of 6Z-9,10-seco-3,20-bis(ethylenedioxy)-5(10),6,8-pregnatriene and 34.6% (=6.92 g) of 9β,10α-3,20-bis(ethylenedioxy)-5,7-pregnadiene. Yield 75.5% calculated on converted starting material. The solution was worked up by evaporation of tetrahydrofuran, taking up the residue in 300 ml of methyl acetate, and cooling to −25 C. A crystallisate was obtained consisting of 9.08 g of starting material and 0.68 of 9β,10α-3,20-bis(ethylenedioxy)-5,7-pregnadiene. After evaporating the mother liquor and adding methanol, a second crystallisate was obtained consisting of 1.12 g of starting material and 5.10 g of 9β,10α-3,20-bis(ethylenedioxy)-5,7-pregnadiene, so that totally 5.78 g of desired product were obtained. Total yield of crystalline material 63.1% with respect to converted starting material.

EXAMPLE II

Preparation of lumisterol$_2$

According to the conditions described in Example I, 19.9 g of ergosterol in tetrahydrofuran were irradiated with a Q2017 antimony lamp. An irradiation time of 3 hours with the use of the first filter was used, succeeded by 5 hours with the use of the second filter. Finally a solution was obtained, the dissolved substance of which according to HPLC-analysis has the following composition: 53.1% (=10.57 g) of ergosterol, 1.8% (=0.36 g) of previtamin D$_2$, and 37.3% (=7.42 g) of lumisterol$_2$. Yield 79.5% calculated on converted starting material. The solution was worked up by removing tetrahydrofuran via evaporation and dissolving the residue in boiling ethanol. After cooling, 8.08 g of ergosterol were recovered.

2.28 g of ergosterol and 6.33 g of lumisterol$_2$ were obtained from the mother-liquor by means of liquid chromatography.

Yield 66.5% calculated on consumed starting material.

EXAMPLE III

Preparation of lumisterol$_3$

According to the conditions described in Example I, 19.20 g of 7-dehydrocholesterol in tetrahydrofuran were irradiated with a Q 2017 antimony lamp. A radiation time of 2 hours with the use of the first filter was used, succeeded by 4 hours with the use of the second filter. Finally a solution was obtained, the dissolved substance of which according te HPLC-analysis has the following composition: 47.0% (=9.02 g) of 7-dehydrocholesterol, 2.5% (=0.48 g) of previtamin D$_3$, and 48,0% (=9.22 g) of lumisterol$_3$. Yield 91% calculated on converted starting material.

EXAMPLE IV

Preparation of 9β,10α-3,20-bis(ethylenedioxy)-5,7-pregnadiene 23.0 g of 6Z-9,10-seco-3,20-bis(ethylenedioxy)-5(10),6,8-pregnatriene (previtamin D analogon) were dissolved in 3.5 liters of methyl acetate. The solution was then irradiated with a Q2017 antimony lamp for 8.5 hours while cooling and in a nitrogen atomosphere.

The light below 303 nm was absorbed by a filter.

Finally a solution was obtained, the dissolved substance of which according to HPLC-analysis has the following composition: 4.5% (−1.04 g) of starting material, 29.2% (=6.72 g) of 9α,10β-3,20-bis(ethylenedioxy)-5,7-pregnadiene, and 48,9% (=11.25 g) of 9β,10α-3,20-bis(ethylenedioxy)-5,7-pregnadiene. The solution was worked up by evaporation down to 350 ml and cooling to −25° C. A crystallisate consisting of 3.30 g of 9β,10α-3,20-bis(ethylenedioxy)-5,7-pregnadiene and 4.74 g of 9β,10α-3,20 bis(ethylenedioxy)-5,7-pregnadiene was obtained. After evaporating the mother liquor and adding methanol, a second crystallisate was obtained consisting of 0.97 g of 9α,10β-3,20-bis(ethylenedioxy)-5,7-pregnadiene and 7.11 g of 9β,10α-3-20-bis(ethylenedioxy)-5,7-pregnadiene. 16.12 g (70.1%) of crystalline ring-closed product (5,7-diene) were obtained, 65% of which has the 9β,10α- and 35% has the 9α,10β-configuration.

EXAMPLE V

Preparation of lumisterol₃

According to the conditions described in Example IV, 25.1 g of previtamin D₃ in tetrahydrofuran were irradiated with a Q2017 antimony lamp.

Finally a solution was obtained, the dissolved substance of which according to HPLC-analysis has the following composition: 4.5% (=1.13 g) of previtamin D₃, 19.4% (=4.87 g) of 7-dehydrocholesterol, and 76.5% (=19.2 g) of lumisterol₃.

EXAMPLE VI

Preparation of lumisterol₃

According tot the conditions described in Example IV, 7.09 of tachysterol₃ in tetrahydrofuran were irradiated with a Q2017 antimony lamp.

Finally a solution was obtained, comprising according to HPLC-analysis: 21.6% (=1.51 g) of 7-dehydrocholesterol and 75.0% (−5,25 g) of lumisterol₃. Previtamin D₃ and tachysterol₃ could not be detected.

EXAMPLE VII

Preparation of 9β,10α-3,20-bis(ethylenedioxy)-5,7-pregnadiene 40.0 g of 9α,10β3,20-bis(ethylenedioxy)-5,7-pregnadiene were dissolved in 4 liters of methyl acetate. The resulting solution was then irradiated with a 1500 W medium pressure mercury lamp (Philips HOV, reg. trademark) while cooling and in a nitrogen atmosphere. A filter was used which absorbs all the light below a wavelength of 280 nm.

After two hours a solution was obtained, the dissolved substance of which according to HPLC analysis was composed as follows: 66% (=26.6 g) of starting material, 22.9% (9.2 g) of 6Z-9,10-seco-3,20-bis(ethylenedioxy)-5(10),6,8-pregnatriene and 9.9% (=4.0 g) of 9β,10α-3,20-bis(ethylenedioxy)-5,7-pregnadiene.

Then the mercury lamp was replaced by an antimony lamp (Heraeus Q2017, reg. trademark) and a filter solution was applied which absorbs all the light below a wavelength of 300 nm.

The solution was irradiated for 5 hours and again analysed by HPLC, which gave the following composition of the dissolved substance: 69.6% (27.8 g) of starting material, 3.0% (=1.2 g) of 6Z-9,10-seco-3,20-bis(ethylenedioxy)-5(10),6,8-pregnatriene and 22.6% (=9.0 g) of 9β,10α-3,20-bis(ethylenedioxy)-5,7-pregnadiene.

Therefore the yield, based on consumed starting material, was 74%.

We claim:

1. A method of preparing 9β,10α-5,7-diene steroids by irradiating the corresponding 9α,10β-steroids with filtered ultraviolet light, characterized in that the irradiation is carried out with an antimony lamp.

2. A method as claimed in claim 1, characterized in that prior to the irradiation with light of an antimony lamp, the starting steroid is irradiated with a conventional light source producing UV-radiation.

3. A method as claimed in claim 1 or 2, characterized in that the starting steroid is a compound of the general formula

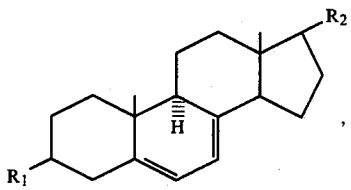

,

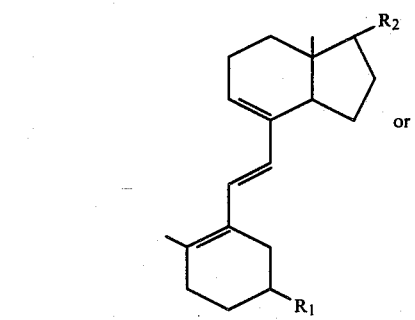

or

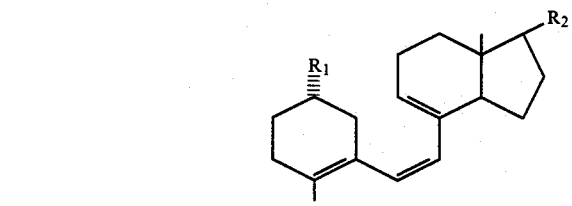

wherein R₁ is a hydrogen atom; an etherified, non-etherified, esterified or non-esterified hydroxy group; or a ketalized or non-ketalized oxo group; and R₂ is a branched or non-branched, saturated or unsaturated hydrocarbon chain having at most 10 carbon atoms which, if desired, is substituted with one or more fluorine atoms, etherified, non-etherified, esterified or non-esterified hydroxy groups, and/or ketalized or non-ketalized oxo groups.

4. A method as claimed in claim 3, characterized in that the starting steroid is ergosterol, 9α,10β-3,20-bis(ethylenedioxy)-5,7-pregnadiene or 7-dehydrocholesterol.

5. A method as claimed in claim 3, characterized in that the starting steroid is previtamin D₃ or 6Z-9,10-seco-3,20-bis(ethylenedioxy)-5(10),6,8-pregnatriene.

6. A method as claimed in claim 3, characterized in that the starting steroid is tachysterol₃ or 6E-9,10-seco-3,20-bis(ethylenedioxy)-5(10),6,8-pregnatriene.

* * * * *